United States Patent
Buettner-Janz et al.

(10) Patent No.: US 9,265,617 B2
(45) Date of Patent: Feb. 23, 2016

(54) PROSTHESIS FOR CERVICAL AND LUMBAR SPINE

(76) Inventors: Karin Buettner-Janz, Berlin (DE); Eiko Buettner, Berlin (DE)

(*) Notice: Subject to any disclaimer, the term of this patent is extended or adjusted under 35 U.S.C. 154(b) by 0 days.

(21) Appl. No.: 13/876,013

(22) PCT Filed: Oct. 6, 2010

(86) PCT No.: PCT/EP2010/064914
§ 371 (c)(1), (2), (4) Date: Mar. 26, 2013

(87) PCT Pub. No.: WO2012/045340
PCT Pub. Date: Apr. 12, 2012

(65) Prior Publication Data
US 2013/0184828 A1    Jul. 18, 2013

(51) Int. Cl.
*A61F 2/44* (2006.01)
*A61F 2/30* (2006.01)

(52) U.S. Cl.
CPC ............... *A61F 2/442* (2013.01); *A61F 2/4425* (2013.01); *A61F 2/4405* (2013.01); *A61F 2002/304* (2013.01); *A61F 2002/308* (2013.01); *A61F 2002/3069* (2013.01); *A61F 2002/30227* (2013.01); *A61F 2002/30247* (2013.01); *A61F 2002/30311* (2013.01); *A61F 2002/30387* (2013.01); *A61F 2002/30393* (2013.01); *A61F 2002/30428* (2013.01); *A61F 2002/30563* (2013.01); *A61F 2002/30604* (2013.01); *A61F 2002/30614* (2013.01); *A61F 2002/30616* (2013.01); *A61F 2002/30652* (2013.01); *A61F 2002/30658* (2013.01); *A61F 2002/30663* (2013.01); *A61F 2002/30665* (2013.01); *A61F 2002/30777* (2013.01); *A61F 2002/30779* (2013.01); *A61F 2002/30805* (2013.01); *A61F 2002/30841* (2013.01); *A61F 2002/30846* (2013.01); *A61F 2002/30848* (2013.01); *A61F 2002/30879* (2013.01); *A61F 2002/30884* (2013.01); *A61F 2002/30896* (2013.01); *A61F 2002/30899* (2013.01); *A61F 2002/443* (2013.01)

(58) Field of Classification Search
CPC ................... A61F 2002/443; A61F 2002/448; A61F 2002/4485; A61F 2/44; A61F 2/4425
USPC ............................................ 623/17.11–17.16
See application file for complete search history.

(56) References Cited

U.S. PATENT DOCUMENTS

| 5,899,941 | A * | 5/1999 | Nishijima et al. | 623/17.15 |
| 7,235,103 | B2 * | 6/2007 | Rivin | 623/17.13 |
| 8,057,547 | B2 * | 11/2011 | Hurlbert et al. | 623/17.14 |

(Continued)

*Primary Examiner* — Eduardo C Robert
*Assistant Examiner* — Michelle C Eckman
(74) *Attorney, Agent, or Firm* — 24IP Law Group; Timothy R DeWitt

(57) ABSTRACT

The present invention relates to an intervertebral disc prosthesis for the total replacement of an intervertebral disc of the cervical or lumbar spine. The prosthesis provided by the invention is intended for coupled physiological motion within the disc space. The design of the disclosed prosthesis is based on an inlay positioned within the articulation area of two adjacent sliding partners and provides the advantage of comprising a ball and socket shaped articulation area, which enables limitation of rotation around the sagittal, frontal and longitudinal axis. The inlay is protected against luxation due to its position within a recess of one of the adjacent sliding partners. An additional protuberance going through the inlay is protecting against luxation of the adjacent sliding.

22 Claims, 21 Drawing Sheets

(56) References Cited

U.S. PATENT DOCUMENTS

| | | | |
|---|---|---|---|
| 2003/0074072 A1* | 4/2003 | Errico et al. | 623/17.14 |
| 2004/0133278 A1* | 7/2004 | Marino et al. | 623/17.14 |
| 2007/0233262 A1* | 10/2007 | Arnin et al. | 623/17.15 |
| 2007/0250170 A1* | 10/2007 | Moumene et al. | 623/17.15 |
| 2008/0058940 A1* | 3/2008 | Wu et al. | 623/17.15 |
| 2008/0234686 A1* | 9/2008 | Beaurain et al. | 606/90 |
| 2008/0300685 A1* | 12/2008 | Carls et al. | 623/17.11 |
| 2009/0076615 A1* | 3/2009 | Duggal et al. | 623/17.16 |
| 2009/0082867 A1* | 3/2009 | Sebastian Bueno et al. | 623/17.16 |
| 2009/0138090 A1* | 5/2009 | Hurlbert et al. | 623/17.16 |
| 2009/0281628 A1* | 11/2009 | Oglaza et al. | 623/17.15 |
| 2010/0030338 A1* | 2/2010 | Simon | 623/17.16 |
| 2010/0222885 A1* | 9/2010 | Hurlbert et al. | 623/17.16 |
| 2012/0172988 A1* | 7/2012 | Berger et al. | 623/17.16 |

\* cited by examiner

Fig. 2
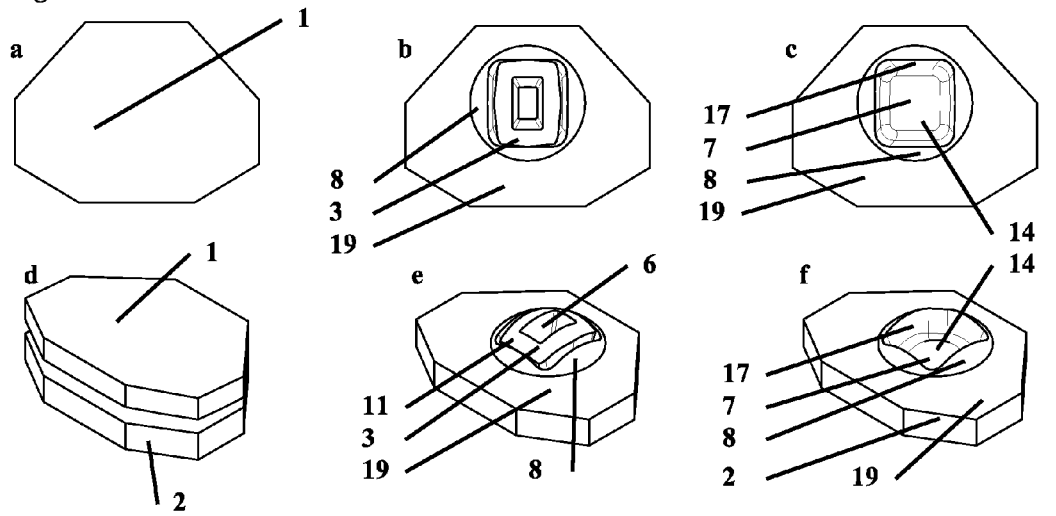
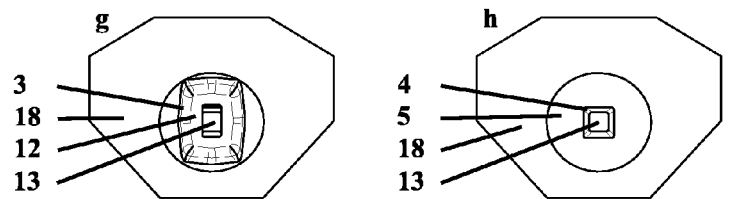
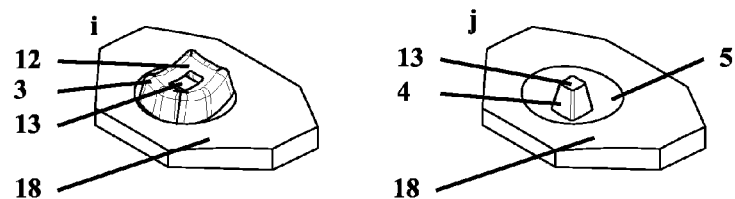
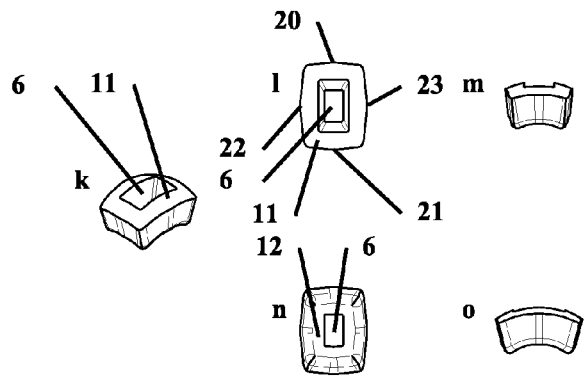

Fig. 4
a 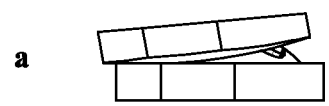
b 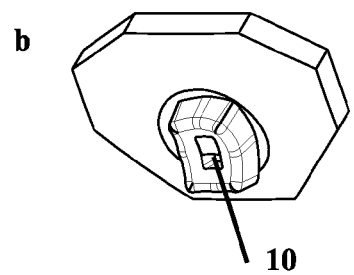
c, d 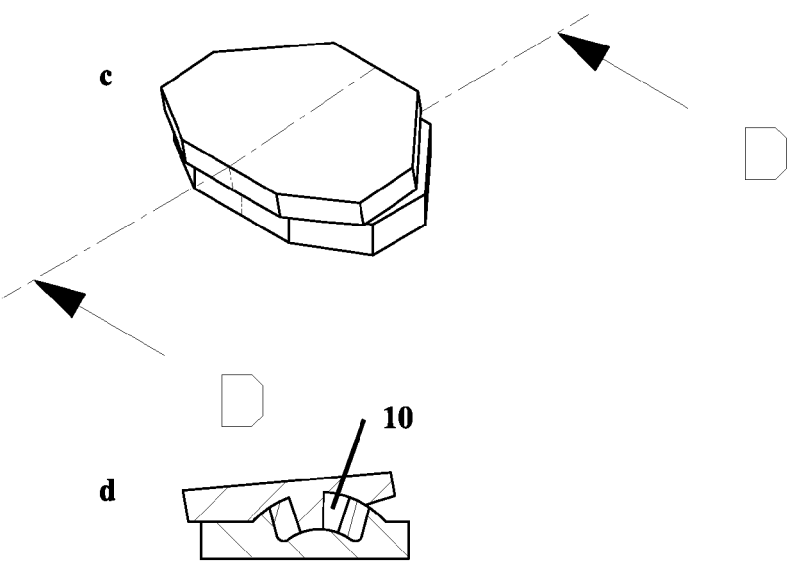
SECTION D-D

SECTION F-F

Fig. 9
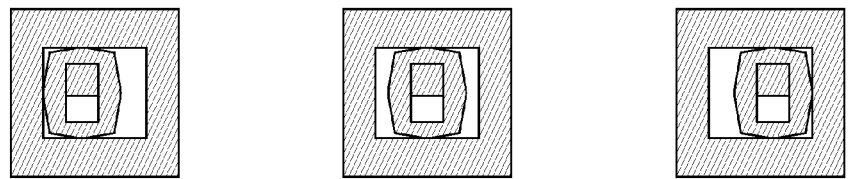
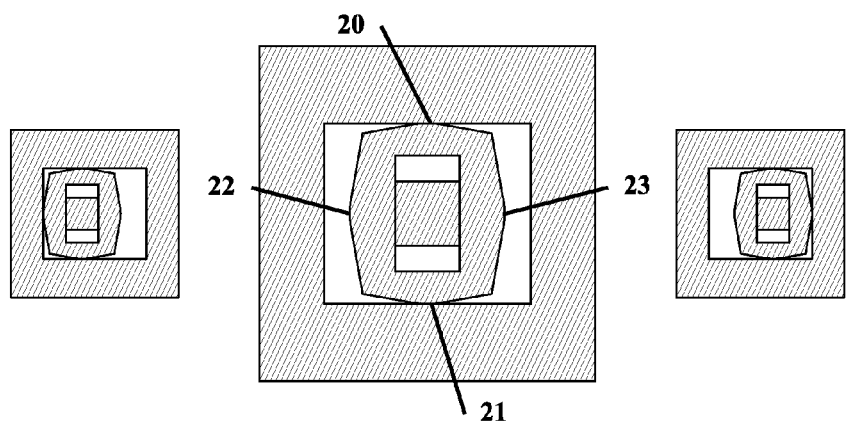
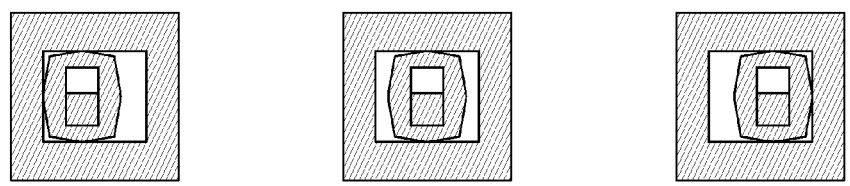
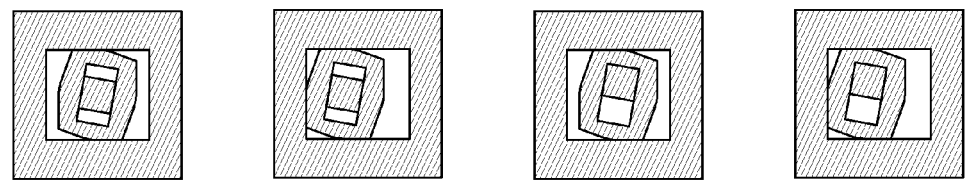
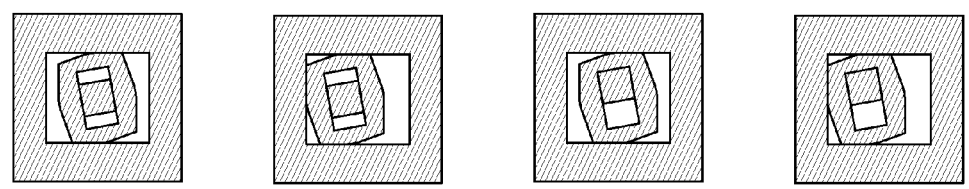

Fig. 10
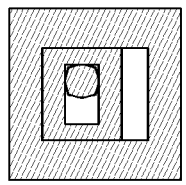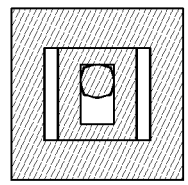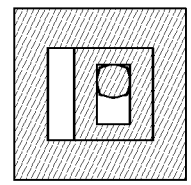
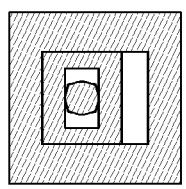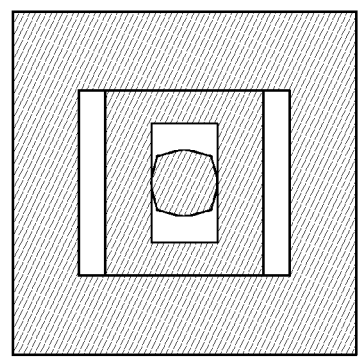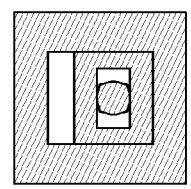
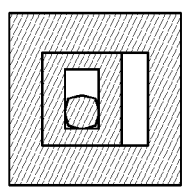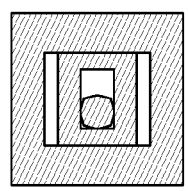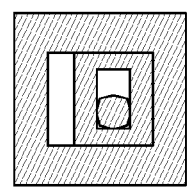
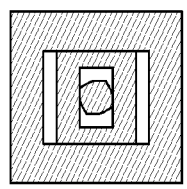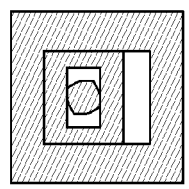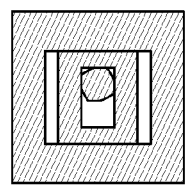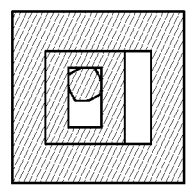
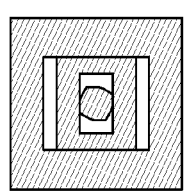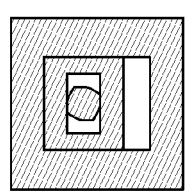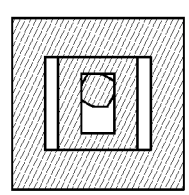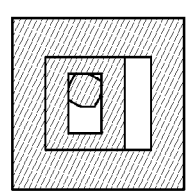

Fig. 11
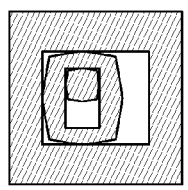
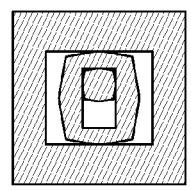
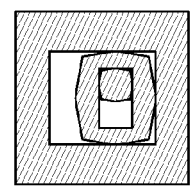
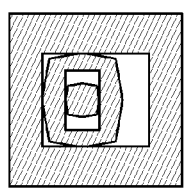
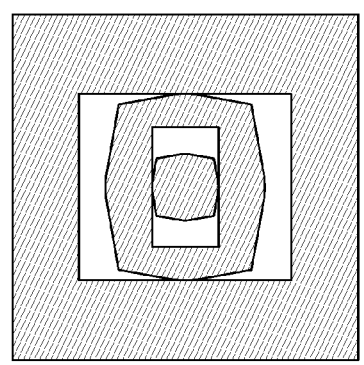
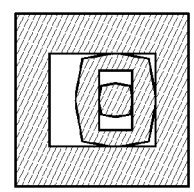
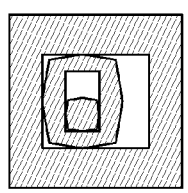
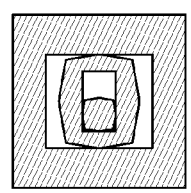
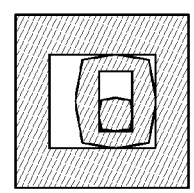
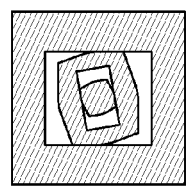
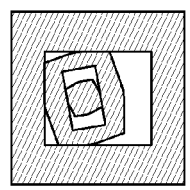
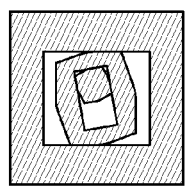
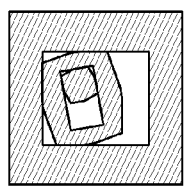
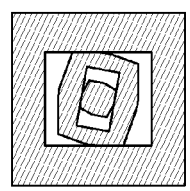
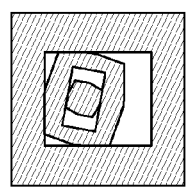

SECTION G-G

Fig. 14
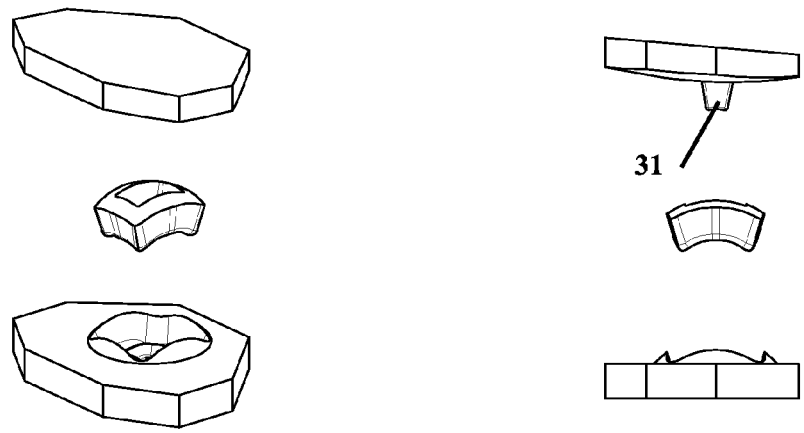
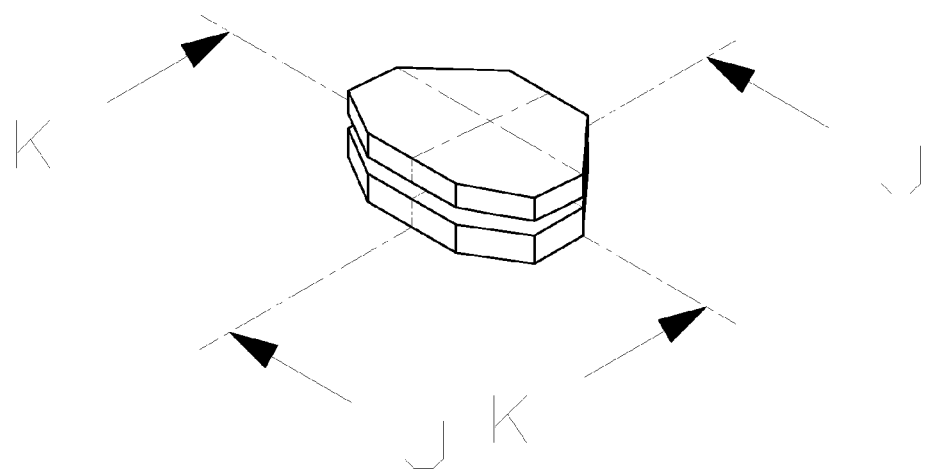
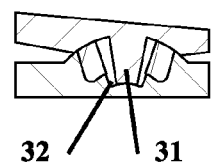 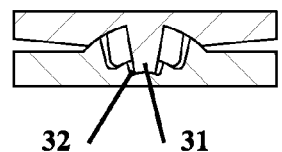
SECTION J-J    SECTION K-K

Fig. 15
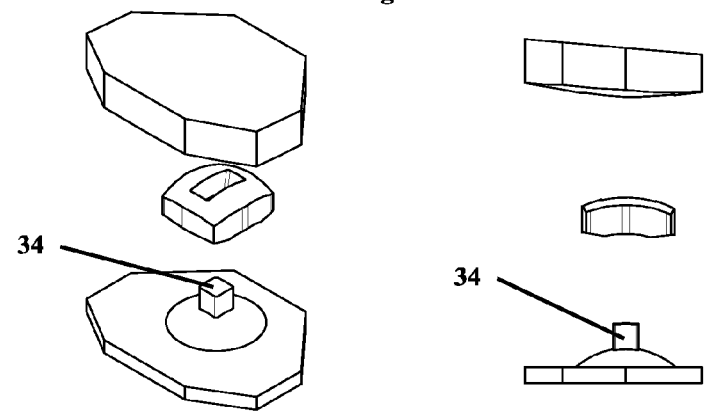
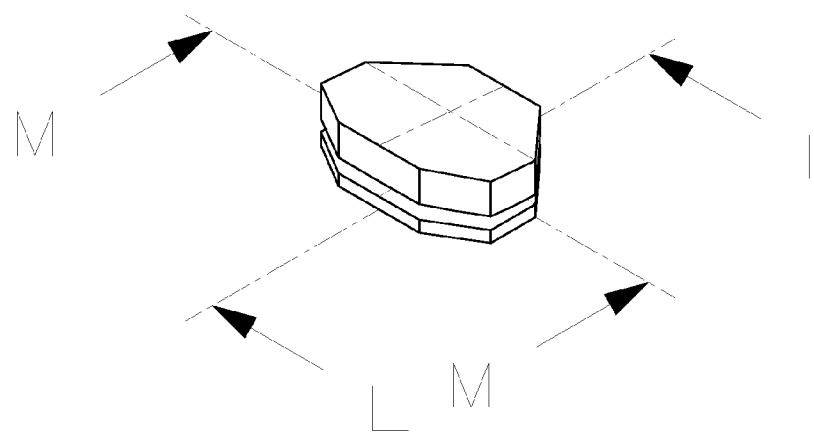
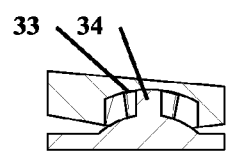 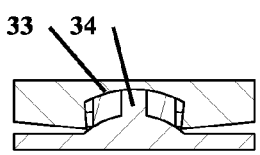
SECTION L-L        SECTION M-M
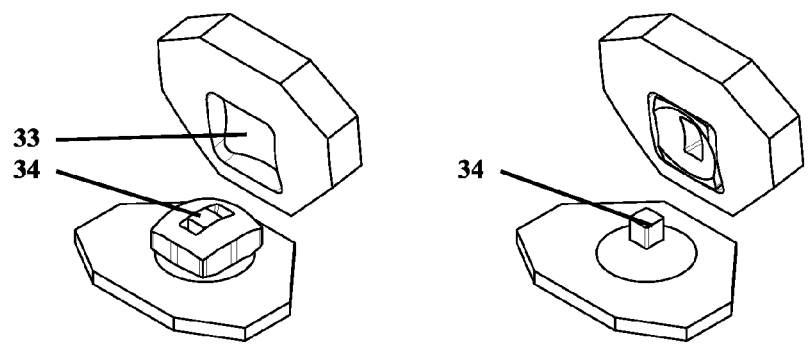

Fig. 16
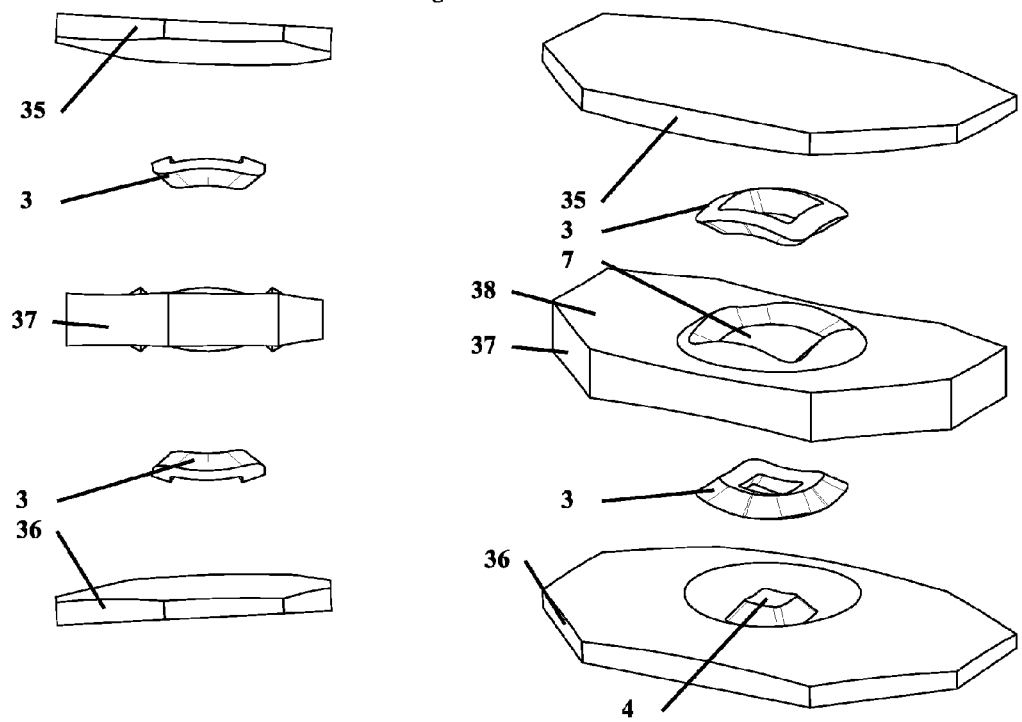
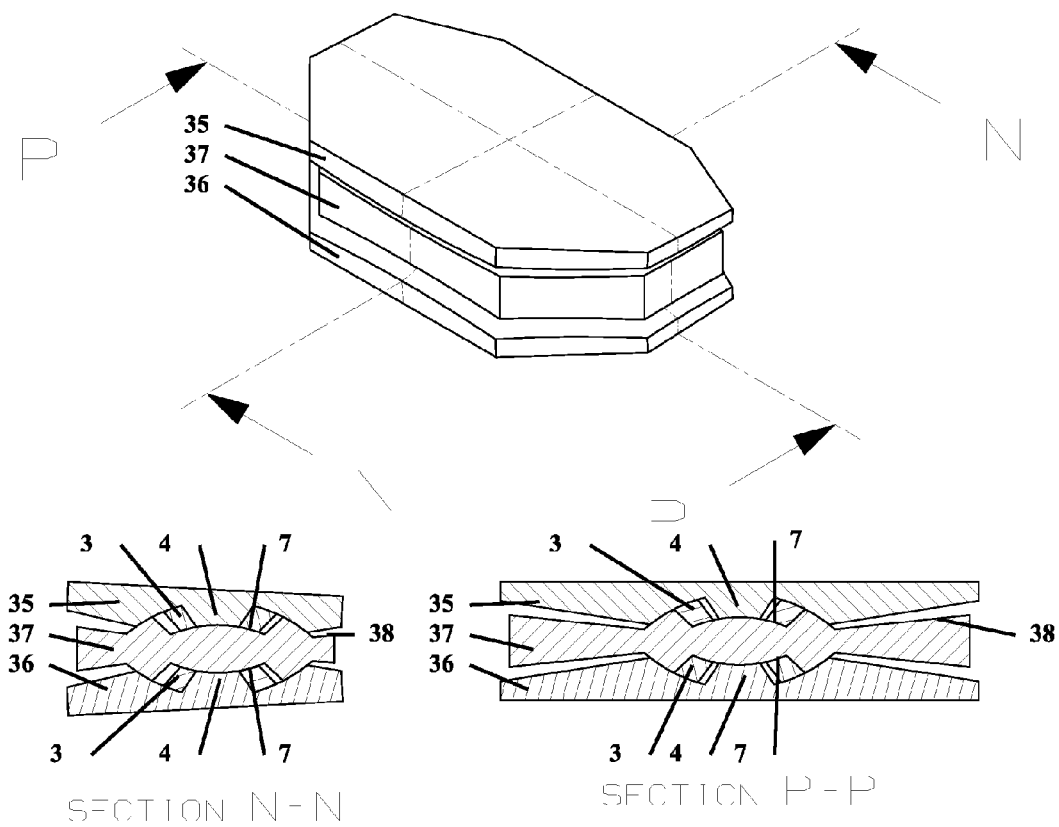
SECTION N-N SECTION P-P

Fig. 17
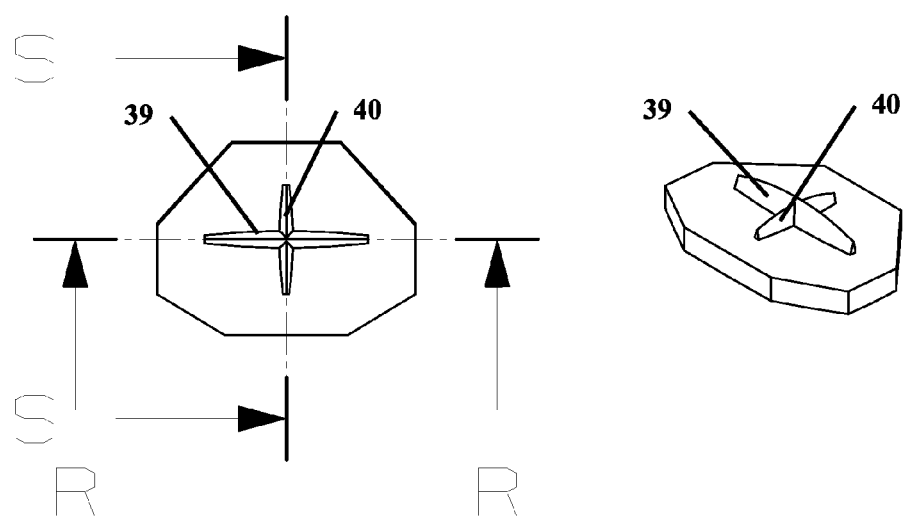

PROSTHESIS FOR CERVICAL AND LUMBAR SPINE

FIELD OF THE INVENTION

The present invention relates to an intervertebral disc prosthesis for the total replacement of an intervertebral disc of the cervical and lumbar spine.

BACKGROUND OF THE INVENTION

The idea of function-retaining artificial replacements for intervertebral discs is younger than replacements of artificial joints of extremities, but nonetheless more than 50 years old [Büttner-Janz, Hochschuler, McAfee (Eds.): The Artificial Disc. Springer Verlag, Berlin, Heidelberg, New York 2003]. It is a response to biomechanical considerations, unsatisfactory results of fusion surgeries of the cervical and lumbar spine, disorders adjacent to fused motion spinal segments, and the development of new materials with better sliding properties and greater longevity.

By means of function-retaining disc implants it is possible to avoid fusion surgery, i.e. to maintain, to restore or to improve the mobility within the intervertebral disc space. In an in-vitro experiment it is possible to achieve a normalization of the biomechanical properties of the spinal motion segment to a large extent through the implantation of an artificial intervertebral disc Presently, many intervertebral function retaining disc implants are clinically used. Total disc replacement on the lumbar spine started with the CHARITE Artificial Disc, later followed by the PRODISC, the MAVERICK, the FLEXICORE, the MOBIDISC, the KINEFLEX; the ACTIV L, the XL-TDR, the DYNARDI, the PHYSIO-L, the INMOTION, the M6L, the FREEDOM and further disc prostheses. On the cervical spine many function retaining disc implants are known as well, as for example the BRYAN, the PRESTIGE, the PRODISC-C, the KINEFLEX C, the MOBIC, the ACTIV C, the DISCOCERV, the DISCOVER, the PCM, the CERVICORE, the M6C, the GALILEO, the GRANVIA, the NUNEC, and the BAGUERA C.

There are different classifications of cervical and lumbar total disc prostheses, according to the number of articulation partners, and according to biomechanical considerations and direct function-related conditions within the cervical as well as the lumbar intervertebral space. At present, prostheses with two, one or no articulation surface(s) are used. Depending on the number of functional components and the material, the prostheses have biomechanically a fixed or mobile centre of rotation. Whereas prostheses with two sliding surfaces having a mobile centre of rotation are more physiologically designed, prostheses with only two functional related partners and one sliding surface are able to better stabilize the spine in multi-segmental implantations.

The artificial discs can be implanted via a ventral, ventro-lateral, lateral or dorsal approach. Depending on the approach the artificial discs are constructed with different shape, size and means for instruments. Different sizes of disc prostheses base on the size of the prosthetic plates, different heights on the height of the prosthetic components, and different angles of lordosis on the angles of prosthetic components. The trapezium natural disc shape is primarily responsible for the lordosis of the lumbar and cervical spine, further the vertebral bodies contribute to a minor extent to the lordosis. During prosthetic replacement of an intervertebral discs the lordosis should be maintained or reconstructed. A hyperlordotic angle of the operated spinal segment, because in the longer run a painful facet joint degeneration can be expected, is to avoid. A hyperlordotic disc space is a pre-condition for reduced segmental range of motion as well. In that case the target prevention of the adjacent motion segment against disc degeneration can not be fulfilled.

The common material for sliding disc implants is metal in combination with polyethylene or metal-to-metal. In the meantime partly new materials for total discs are used including for coating of the disc implants to achieve the opportunity for MRI diagnostics as well as better sliding properties of the implants, to avoid any revision surgery.

A healthy intervertebral disc allows in its interaction with other elements of a functional spinal unit limited motion at different ranges of motion in extension and flexion as well as in lateral bending to the right and left and in axial rotation. Motion to the front and back is combined with rotational motion, and side motion is combined with other motion directions; it is a matter of so called "coupled motion". The motion amplitudes of healthy intervertebral discs are different, with respect to extension (bending back) and flexion (bending forward) as well as to the lateral bending to the right and left and axial rotational motion. Although of common basic characteristics, there are differences between the motion amplitudes of the cervical and lumbar spine as well.

All prostheses for total disc replacements which are currently clinically used do not cover completely the natural function of a cervical or lumbar motion segment, including the natural range of motion. In the long-term experience facet joint degeneration and facet joint disease at the same level of disc implantation and/or in the neighbourhood may occur as a result of prosthetic disc hyper-mobility and connected dysfunction of the facet joints. Abrasion of the facet joints (arthritis, spondylarthritis) may occur, with a formation of osteophytes. As a result the irritation of neural structures is possible as well as directly caused pain in the facet joints.

There is so far no evidence that shock absorption is needed within the spine to save tissue or specific anatomical structures; the facet joints are usually not horizontally loaded. The main function of shock absorption seems to enable a motion within the disc space because the natural disc does not have typical joint partners like ball and socket. By having the shock absorption of the disc the intervertebral angle can be changed without reducing significantly the disc height at same time.

Some disc prostheses include shock absorption to its function, but again without to simulate the segmental physiological range of motion. Postoperatively kyphotic intervertebral disc spaces with dangerous potential for facet joint hyper-mobility and facet joint degeneration and disease can be observed. So the original aim of a function retaining disc replacement to achieve a painless or pain free stabilization of the spinal motion segment by implantation of the disc prosthesis is not yet fulfilled in the long run.

The longest experience exists with the Charite prosthesis, which is the subject matter of DE 35 29 761 C2 and U.S. Pat. No. 5,401,269 specifications. This prosthesis was developed in 1982 by Dr. Schellnack and Dr. Büttner-Janz at the Charite University Hospital in Berlin and was later on named SB Charité prosthesis. In 1984 the first surgery took place. The intervertebral disc prosthesis was further developed into model III and has been implanted worldwide (DE 35 29 761 C2, U.S. Pat. No. 5,401,269) since 1987; it is replaced by the INMOTION, with same functional principle of a three-part metal to polyethylene prosthesis, with two identical spherical articulation surfaces and a mobile centre of rotation.

Due to a simultaneous translation movement of adjacent vertebrae, the centre of rotation changes its position constantly in case of inconstant centre of rotation. The prosthesis according to DE 35 29 761 C2 shows a construction which differs relative to other available types of prostheses which are build like a ball and socket joint and as a result move around a defined localized centre of rotation. By virtue of the three-part assembly of the prosthesis according to DE 35 29 761 C2, with two metallic endplates and the interpositioned freely mobile polyethylene sliding core, the course of motion of a healthy intervertebral disc of the human spine is mimicked as far as possible, however without the exact motion amplitudes in the specific motion directions.

There is a need for an intervertebral disc prosthesis for the cervical and lumbar spine that enables physiological motion of high quality and physiological quantity. The three-dimensional range of motion within the intervertebral space should mimic the coupled motion of a natural disc, including the physiological translation in the sagittal and frontal view. In case of special anatomical and/or biomechanical local conditions or in case of revision surgery, a disc prosthesis is sometimes needed which does not allow motion to all directions postoperatively. A disc prosthesis for implantation via a lateral approach is needed as well.

In case of any problem after total disc replacement, finally a fusion surgery is often carried out, sometimes including removal of the disc prosthesis. Especially in disc prostheses with big anchoring means for fixation on the vertebral body the removal of the implanted and ingrown disc prosthesis leads to the need of bone removal at same time to make the explantation of the disc prosthesis possible. Depending on that issue, a combined usable total disc prosthesis is needed for preservation of motion and if needed for fusion surgery according the surgeon's decision pre- or intraoperatively, to exchange a prosthetic component without removal of the fixed prosthetic plates for having no intervertebral motion postoperatively.

There are only a very few prostheses with luxation-protected components known, as for example the FLEXICORE. Having a prosthesis which also includes physiological translation and which avoids any luxation of components at e.g. a whiplash after accidents via its desing or construction, would be a big new advantage of total disc replacement, allowing more sportive activities or even surgeries on pilots.

SUMMARY OF THE INVENTION

The present disclosure provides an intervertebral disc prosthesis for the total replacement of an intervertebral disc within the cervical or lumbar spine, comprising at least one sliding partner adapted to firmly assemble with its outer surface with an upper vertebral body and a further adjacent sliding partner adapted to firmly assemble with its outer surface with a lower vertebral body, and the adjacent sliding partners articulate via articulation surfaces on their facing inner sides, comprising an articulation area with a convexity on one sliding partner and a concavity on the other sliding partner, wherein a first of the adjacent sliding partners has a recess with a bottom surface and four side surfaces, wherein the recess is positioned within the convexity or concavity of the first sliding partner, and a second of the adjacent sliding partners, which articulates with the first sliding partner has a protuberance with four side surfaces and a tip surface, wherein the protuberance is arranged within the concavity or convexity of the second sliding partner, and an inlay comprises a cut-out for acceptance of the protuberance, wherein the inlay is positioned within the recess of the first of the adjacent sliding partners, and the inlay has an upper convex or concave articulation surface surrounding the cut-out, having an identical radius of curvature with the convex or concave articulation surface of the first of adjacent sliding partners, and a lower concave or convex articulation surface surrounding the cut-out, having an identical radius of curvature with the concave or convex articulation surface of the bottom of the recess of the first of adjacent sliding partners, and four outer side surfaces comprising an outer perimeter of the inlay facing the four side surfaces of the recess of the first of the adjacent sliding partners, and four inner side surfaces comprising an inner perimeter of the inlay facing the four side surfaces of the protuberance of the second of the adjacent sliding partners, wherein a range of motion between the first and second of the adjacent sliding partners in relation to each other around a sagittal, frontal and longitudinal axis is defined by the radius of curvature of the convexity and concavity, the size and shape of the recess, of the inlay, of the cut-out and of the protuberance, and the size of the space between the side surfaces of the recess and the outer perimeter of the inlay and/or between the inner perimeter of the inlay and the side surfaces of the protuberance.

At least one articulation surface can be partly or completely surrounded by an edge to maximize the motion limiting contact area at final range of motion to each direction in the sagittal and frontal axis.

The edge surrounding at least one articulation surface shall be made of a flexible material enabling soft limitation at a final range of motion to each direction in the sagittal and frontal axis.

The shape of the recess, of the outer and inner perimeter of the inlay and of the protuberance shall be rectangular, round, cylindrical, pyramidal, conical including a truncated pyramid and conus, or a combination of the afore mentioned shapes. The shape of the side surfaces of the recess, the shape of the side surfaces comprising the outer and inner perimeter of the inlay and the shape of the side surfaces of the protuberance shall be plane, curved, angled or round or a combination thereof.

Convexity and corresponding concavity can have a spherical, cylindrical, torus-like, helical and/or conical shape or a combination thereof, and convexity and corresponding concavity can have identical or different radii of curvature.

It is further intended that size and shape of the recess and of the outer perimeter of the inlay can be constructed in such a manner that rotation of adjacent sliding partners around either the sagittal or frontal axis is possible. Size and shape of the recess and of the outer and inner perimeter of the inlay can also be constructed in such a manner that additionally a limited rotation around the longitudinal axis is possible.

In a further embodiment of the present disclosure, size and shape of the inner perimeter of the inlay and of the protuberance can be constructed in such a manner that rotation of adjacent sliding partners around either the sagittal or frontal axis is possible. Size and shape of the inner perimeter of the inlay and of the protuberance can also be constructed in such a manner that additionally a limited rotation around the longitudinal axis is possible.

It is further intended that the shape of the recess and the outer perimeter of the inlay and/or the shape of the inner perimeter of the inlay and the protuberance may allow unlimited rotation around the longitudinal axis.

Two opposing side surfaces of the protuberance can be in a form-fitting manner in contact with two opposing side surfacess of the inner perimeter of the inlay and/or two opposing side surfaces of the outer perimeter of the inlay can be in a form-fitting manner in contact with two opposing side surfaces of the recess.

The tip surface of the protuberance may be concave- or convex-shaped with a radius of curvature corresponding to the concave or convex curvature of the bottom surface of the recess of the first of the adjacent sliding partners, enabling the articulation of tip and bottom surface.

The tip surface of the protuberance may also be articulating with a surface of a hole arranged below the bottom surface of the recess, and the tip surface of the protuberance may have a radius of curvature corresponding to the facing radius of curvature of the bottom surface of the hole.

It is intended that each sliding partner and/or the inlay comprise the same or different material or are coated with the same or different material.

Each sliding partner and/or the inlay may be constructed in one piece or firmly, but reversibly assembled of at least two pieces.

In a further embodiment of the present disclosure, the inlay and/or at least one of the sliding partners or a part of it can be made of a flexible material to damp an intervertebral shock or applied load.

The upper and/or lower sliding partner may have on their outer surfaces for assembly with a vertebral body at least one cross-shaped anchor, optionally in combination with anchoring teeth.

It is further intended that the cross-shaped anchor and/or the outer surfaces of the upper and lower sliding partner for assembly with a vertebral body can be means or have means for an instrument to hold the prosthesis during implantation and explantation.

In a further embodiment of the present disclosure a middle sliding partner with an upper and lower articulation surface is arranged between the inner sides of the upper and lower sliding partner, with the upper articulation surface of the middle sliding partner articulating with the articulation surface of the facing inner side of the upper sliding partner and the lower articulation surface of the middle sliding partner articulating with the articulation surface of the facing inner side of the lower sliding partner, resulting in an upper and a lower articulation area, wherein an inlay is arranged within upper and/or lower articulation area and an articulation area with inlay is constructed as specified above. The articulation areas above and below the middle sliding partner may be constructed equally or different.

DETAILED DESCRIPTION OF THE INVENTION

The prosthesis provided by the invention is intended for primary total disc replacement enabling coupled physiological motion within the disc space between adjacent vertebrae via a ventral, ventro-lateral or lateral approach. The prosthesis is also intended for revision surgeries after former function retaining disc implantations, by insertion of a complete new disc prosthesis or by replacement or exchange of the inlay, if needed without for example lateral bending to the right and/or left postoperatively or with exclusion of any postoperative motion.

The inlay of a prosthesis according to the present disclosure is protected against luxation due to its position within a recess of one of the adjacent sliding partners. An additional protuberance going through the inlay is protecting against luxation of the adjacent sliding partners.

A prosthesis according to the invention comprises basically at least three parts or components, namely two sliding partners and one inlay. The arrangement of a middle sliding partner between the upper an lower sliding partner results in a prosthesis with four or five parts, namely three sliding partners and one or two inlays, depending on the arrangement of an inlay within the upper and/or the lower articulation area.

With respect to the description and depiction of the presented invention an "articulation area" comprises facing articulation surfaces of adjacent sliding partners, which come into contact or articulate with each other. Thus, an articulation area comprises at least two articulation surfaces of adjacent sliding partners. Within the meaning of the present disclosure the parts of the prosthesis articulate via their convex and concave surfaces, comprising the convex and concave parts of the sliding partners, the upper and lower side of the inlay as well as the tip surface of the protuberance and the bottom surface of the recess or the surface of a hole below the bottom surface. The term articulation surface is synonymous with the term sliding surface.

The side surfaces of the recess, the side surfaces of the outer and inner perimeter of the inlay and the side surfaces of the protuberance do not articulate within the meaning of the present disclosure, although they are movable and get in contact or may slide onto each other. These surfaces and the spaces between them are used to determine the range of motion of the prosthesis in order to allow or prevent rotation around either the sagittal, frontal or longitudinal axis. So for example rotation around the frontal axis namely lateral bending to right and left can be excluded, when at same time rotation around the sagittal axis as extension and flexion movement and around the longitudinal axis as axial rotation movement is still allowed in a physiological range of motion. A prosthesis allowing unlimited rotation around the longitudinal axis is also within the scope of the disclosure. In order to achieve no limitation of motion around the longitudinal axis, the shape of the side surface of at least the recess and of the outer perimeter of the inlay, or of the inner perimeter of the inlay and of the protuberance has to be circular, wherein all adjacent side surfaces can have a circular shape as well.

Two-dimensional surface contacts refer to at least two surfaces that come in contact as they have corresponding shapes so that not only punctual or linear contacts take place. This means that a surface does not have to be plane, but shall also have a curved form or a combination of plane and curved as long as a two-dimensional contact of the surfaces will be achieved at rotation around the respective axis, including at maximum possible rotation.

The three spatial axes shall be defined as "sagittal rotational axis" for the extension and flexion function within the disc space, going from the front to the back through the body or vice versa. The rotation around the sagittal axis is in the dorsal and ventral (dorso-ventral) direction. The bending function to the right and left side of the disc space is performed around the "frontal rotational axis" going from the right to the left of the body or vice versa. The "longitudinal axis" is for the right/left axial rotation, meaning the rotation around the vertical axis running in cranio-caudal direction of the body. This rotation is also designated as "axial rotation".

With respect to the present invention the three cutting planes shall be defined by the following terms: A "sagittal section" or a "sagittal view" describes a view from lateral, because the cutting plane runs vertically from the front to the back or vice versa.

The term "frontal" is synonymous with "ventral" and "anterior" and the term "back" with "dorsal" and "posterior". A "frontal section" or the "frontal view" is a vertical section from the right lateral side to the left lateral side of a body or vice versa The term "lateral" stands for sidewise and latero-lateral means from one side to the other side, from the right to the left or vice versa. Sagittal and frontal sections are vertical sections as they both run in a vertical plane from cranial to caudal of the body and disc space or vice versa, but rotated at 90 degrees to each other. A view in the "transversal plane" or a "transversal section" shows a top-view onto the prosthesis and the cutting plane of the endplate of a vertebral body is a horizontal section.

Both, a cutting plane or a rotation axis can be located or shifted centrally, right or left laterally, dorsally, ventrally, caudally or cranially. Additional cutting planes and rotation axes can be angled to each other and do not necessarily have to be perpendicular to each other.

The term "corresponding", with respect to articulating sliding surfaces or side surfaces designates not only congruent convexities and concavities or other facing sliding surfaces, but also convex and concave or otherwise shaped surfaces with tolerances between each other, thus designating articulation and other sliding surfaces, which are not completely congruent. The chosen materials and shapes can cause such "deviations" or tolerances regarding the articulation or other facing and sliding surfaces of corresponding articulating and sliding components on the one hand. On the other hand it may also be intended that articulating and other facing and sliding surfaces are not totally congruent, for instance in order to define directly the maximum possible or a limited rotation or motion of the articulating sliding partners and other parts of the prosthesis or to allow abrasion to be transported out of the articulating surfaces and side surfaces. Such tolerances may also be useful to transport body fluids or other material through the surfaces.

Since the number of the three axes of rotation corresponds to the minimal number of the three articulation directions, the prosthesis according to the present invention provides the possibility to define—in the meaning of allowing or preventing—the rotation around each axis by the interaction of the side surfaces of the recess with the surfaces of the outer perimeter of the inlay and/or the surfaces of the inner perimeter of the inlay with the side surfaces of the protuberance. Both interactions can be used to define the rotation around the sagittal, frontal and longitudinal axis, but for a limitation of rotation around the longitudinal axis, the use of the interaction between the side surfaces of the recess and the side surfaces of the outer perimeter of the inlay is more suitable. Thus, the shape or design of the mentioned parts of the prosthesis according to the disclosure has only to be adapted to the physiological conditions with respect to one of a dorso-ventral, latero-lateral or right/left and craniocaudal rotational direction, under consideration of a combined or simultaneous translation in the horizontal plane or section.

An edge, as per the invention, indicates an area located between the outer rim of the respective sliding partner and the articulation area. An edge surrounds the articulation area, namely convexity and concavity, completely or partly. The edges of the respective sliding partners run horizontally and/or at an incline and have a plane or curved surface. It is essential for the shape of the surfaces of the edges, that during terminal inclination of the sliding partners towards each other a gap-closure across a maximum possible area between the edges of the sliding partners is achieved. In case that the edges do not have a plane surface, they shall have in any case to be designed in such a way that during gap-closure, a maximum maximal? possible two-dimensional contact arises between them.

An edge does otherwise not necessarily directly begin next to the articulation surface of a sliding partner. It is also within the scope of the present disclosure that there is a transition area or even a gap between articulation surface and surrounding edge.

The contact of edges surrounding at least two facing articulation surfaces shall also not be understood as articulation within the meaning of the present disclosure. Such contacts, although they might comprise sliding and result in a limitation of the range of motion of the particular sliding partners along at least one of the three axes, do not contribute or take place within an articulation area according to the disclosure.

A spherical ball-and-socket joint has no limitation regarding the vertical or axial rotation with respect to the two parts of the joint, but such a joint provides good premises for an optimal uptake of pressure during a gap closure of two-dimensional facing surfaces of two adjacent sliding partners. The present disclosure provides a design for a ball-and-socket joint without an unlimited rotation around the vertical resp. longitudinal axis. The arrangement of an inlay into a recess of the convexity or concavity between two sliding partners permits the limitation of axial, but also of sagittal and frontal rotation.

The design of the disclosed prosthesis makes use of the advantages of a spherical ball- and socket shaped articulation area, but is not restricted to such a shape of the convexity and concavity. Another advantage of a prosthesis according to the disclosure is, that the inlay is protected against luxation due to its position within a recess of convexity or concavity, respectively. It has to be noted that a spherical protuberance is not necessarily a hemisphere but can be derived from a hemisphere by vertically cutting it at two opposing sides or by stretching a hemisphere along one axis.

A prosthesis according to the disclosure enables a coupled motion around at least two of the above defined axes, wherein the degree of motion shall be adapted to the average physiological range of motion within the corresponding segment of the cervical or lumbar spine. The shape of the corresponding limiting elements of the prosthesis shall especially take the facet joints and their degree of maximum range of motion into account, in order to prevent non-natural abrasion, degeneration and disease of the facet joints.

In order to achieve the already mentioned and intended two-dimensional surface contacts, the edges which surround the articulation area play an important role. The limitation of extension, flexion and lateral bending to the right and left may also be limited by surface contacts of edges of adjacent sliding partners, even in combination with the shape of the corresponding components of the articulation area, namely the shape and size of the convexity, the concavity, the inlay and the protuberance. It is also intended that the edges may comprise soft or flexible material to fulfil such a function.

A further non-limiting advantage of an intervertebral disc prosthesis, as per the disclosure, is that, in certain embodiments, in addition to its approximated angles of motion, which come close to the natural degrees of motion, the rotation is limited by contact areas of the side surfaces of the recess and the outer perimeter of the inlay and/or of the the side surfaces of the inner perimeter of the inlay and the side surfaces of the protuberance.

The present invention provides an intervertebral disc prosthesis that can be adapted on segmental pre-conditions by choosing a sliding partner with an appropriate recess, an appropriate inlay and a fitting protuberance of the corresponding sliding partner from a set of existing parts or components.

It is further intended that the articulating and/or side surfaces of the sliding partners may be firmly but reversible fixed to the sliding partners. In case of revision surgery at least the upper and lower sliding partner can stay in place, but the inlay can be changed for further motion retaining or limiting function or if needed for fusion of the spinal segment. If the revision surgery is carried out via a lateral or ventro-lateral approach new parts may be implanted for allowing motion to dorsal and ventral direction as well as craniocaudal axial rotation, but for allowing no lateral bending to avoid an angled disc space in the frontal view.

The prosthesis according to the invention allows also to prevent any motion or rotation of the three parts to each other, by choosing only form-fitting components, so that there is no space between recess and inlay and the cut-out of the inlay is in a form-fitting contact with all four side surfaces of the protuberance. Such a blocking of any motion can be easily achieved by simply exchanging the inlay.

In case that the outer sides of the upper and/or lower sliding partner are angled in a lateral view, a prosthesis according to the disclosure is suitable for the equalisation of a lordosis of the cervical or lumbar spine. In case there is an angle of the outer sides of the upper and/or lower sliding partner in a frontal view, a prosthesis according the disclosure is suitable for equalisation of a scoliotic spinal lumbar or cervical segement.

It is also intended that the centre of rotation can be shifted dorsally for up to 3 mm in order to adapt the centre of rotation to the physiological situation or to compensate a dysfunction within the respective intervertebral space.

BRIEF DESCRIPTION OF THE FIGURES

The invention will be described by figures without being limited to the shown embodiments, the figures show:

FIG. 2 Different top views, perspective and bottom views of a prosthesis

FIG. 4 Prosthesis with maximum flexion

DETAILED DESCRIPTION OF THE FIGURES

Figure 1:
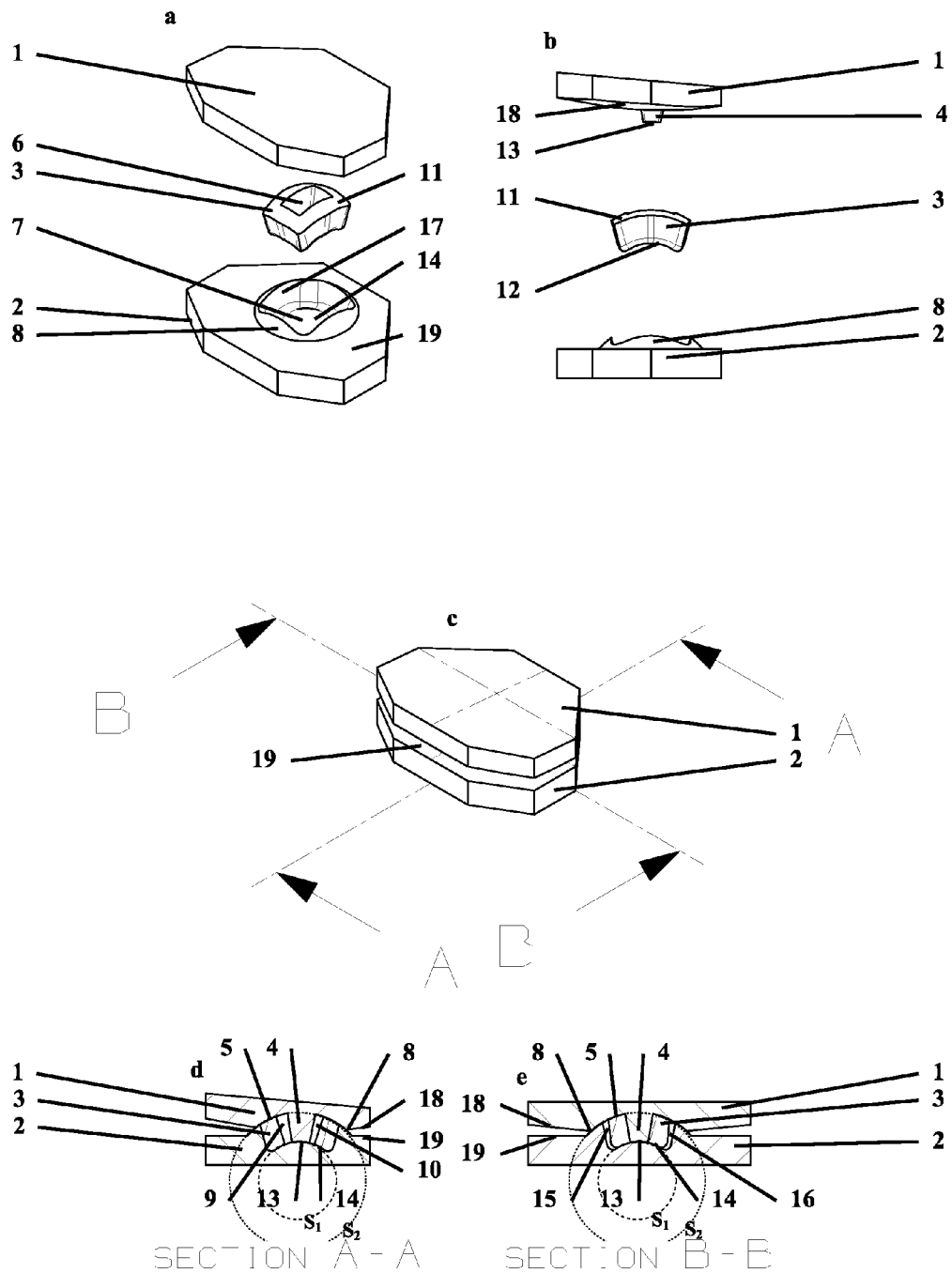
FIG. 1 Different views of a three-component cervical prosthesis
Figure 3:
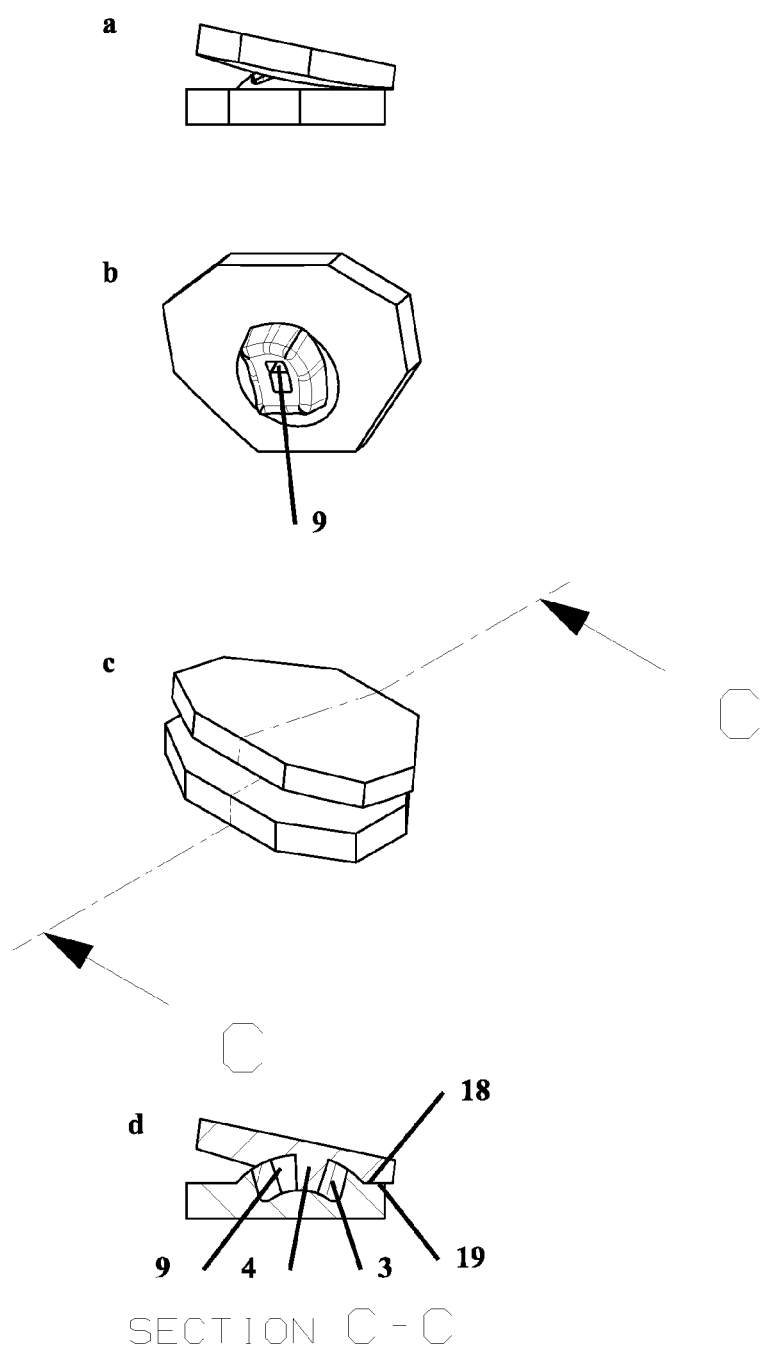
FIG. 3 Prosthesis with maximum extension
Figure 5:
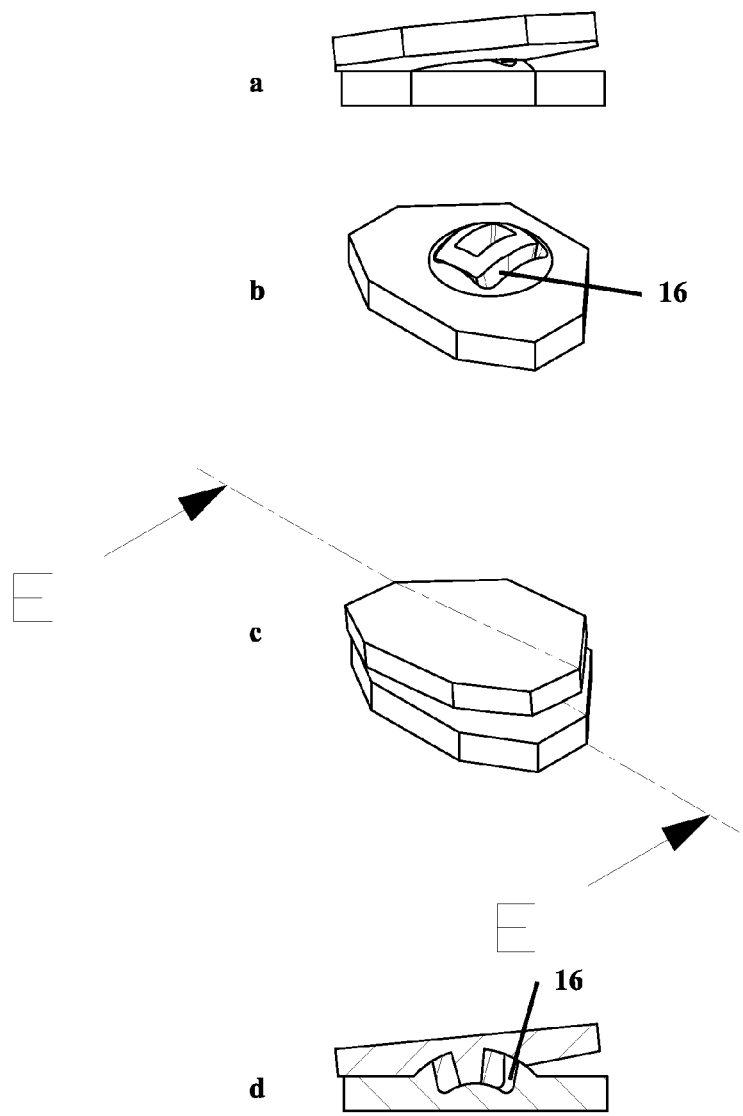
FIG. 5 Prosthesis with maximum bending to the right side
Figure 6:
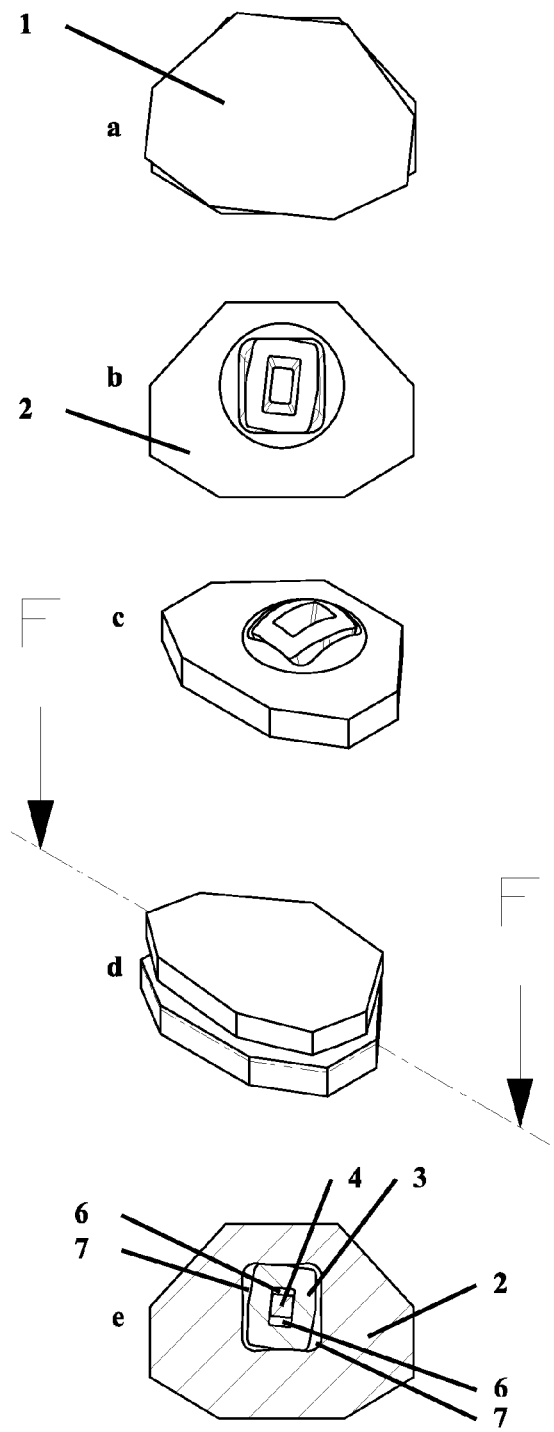
FIG. 6 Prosthesis with maximum axial rotation to the right side

FIG. 1 shows different views of a three-component intervertebral disc prosthesis for the cervical spine. FIG. 1a illustrates an exploded perspective view of the prosthesis, FIG. 1b an exploded side view, and FIG. 1c shows the prosthesis in an assembled status. FIGS. 1d and 1e show sagittal and frontal section views as indicated by the corresponding section lines in FIG. 1c. The prosthesis comprises three distinct parts or components: an upper sliding partner 1, a lower sliding partner 2 and an inlay 3 located in a recess 7 of the lower sliding partner 2. The two section views show how the three components of the prosthesis are assembled. The upper sliding partner 1 has a protuberance 4 with its basis or origin in the concavity 5 of the inner side of the upper sliding partner 1 (see also FIGS. 2h and 2j). The protuberance 4 fits into the cut-out of the inlay 6. Both, the inlay 3 and the protuberance 4 are located in the recess 7 that is positioned within the convexity 8 of the inner side of the lower sliding partner 2.

The sagittal section view in FIG. 1d shows that small gaps 9, 10 are situated between the side surfaces of the protuberance 4 and the corresponding facing side surfaces of the inlay 3. Furthermore, the concavity 5 of the upper sliding partner 1, the upper 11 and lower 12 sides of the inlay 3, the tip of the protuberance 13, the convexity 8 of the lower sliding partner 2 and the bottom 14 of the recess 7 all have curved surfaces. Thus, there is the possibility of a limited rotational movement around the sagittal axis between the upper and the lower sliding partner 1, 2, corresponding to extension and flexion of the spinal unit where the prosthesis is implanted. Furthermore, the sagittal section view in FIG. 1d shows that the outer sides of the upper and lower sliding partners 1, 2 are slightly angled, providing an equalisation of the lordosis of the disc space. Anteriorly, the prosthesis is slightly higher than posteriorly. Moreover, FIG. 1d shows that the centre of rotation for extension and flexion is placed posteriorly, towards the physiological centre of rotation of the functional spinal unit.

The frontal section view in FIG. 1e shows a similar assembly. In this embodiment, however, gaps 15, 16 are located between the side surfaces of the outer perimeter of the inlay 3 and the respective facing side surfaces 17 of the recess 7. Thus, there is also the possibility of a limited rotational movement around the sagittal axis between the upper and the lower sliding partner 1, 2, corresponding to lateral bending of the spinal unit where the prosthesis is implanted.

The aforementioned rotational movements are limited by the embodiment of the prosthesis. Obviously, the different rotational movements are stopped as soon as a) the protuberance 4 and the inlay 3 get in touch with each other, b) the inlay 3 gets in contact with the side surfaces 17 of the recess 7, or c) the edge 18 of the upper sliding partner 1 and the edge 19 of the lower sliding partner 2 contact each other.

FIG. 2 depicts different top, perspective and bottom views of the prosthesis in different states of assembly as well as different views of the inlay 3. In FIGS. 2a, 2b and 2c the prosthesis is disassembled step by step. FIG. 2a shows a top view of the entire prosthesis, FIG. 2b shows the inlay 3 and the lower sliding partner 2 and FIG. 2c shows the lower sliding partner 2 alone. FIGS. 2d, 2e and 2f show the same states of assembly in different perspective views. FIG. 2g shows a bottom view of the inlay 3 and the upper sliding partner 1, and FIG. 2h shows the upper sliding partner 1 alone. FIGS. 2i and 2j show the same configurations in two perspective views. FIGS. 2k-2o show perspective, top, front, bottom and side views of the inlay 3.

As can be seen in FIGS. 2b, c, e, f, g-j as well as in 1d and 1e, the upper side 11 of the inlay 3, the convexity 8 of the inner side of the lower sliding partner 2 and the concavity 5 of the inner side of the upper sliding partner 1 have the same radius of curvature. In fact, all three aforementioned surfaces lie on the same sphere $S_2$ as indicated by the dotted circles in FIGS. 1d and 1e. Similarly, the lower side 12 of the inlay 3, the bottom 14 of the recess 7 and the tip of the protuberance 13 have the same radius of curvature. All three surfaces are located on the same sphere $S_1$ as indicated by the dotted circles in FIGS. 1d and 1e. Obviously, $S_1$ has a smaller radius than $S_2$, but both spheres have the same centre point.

Figure 21:
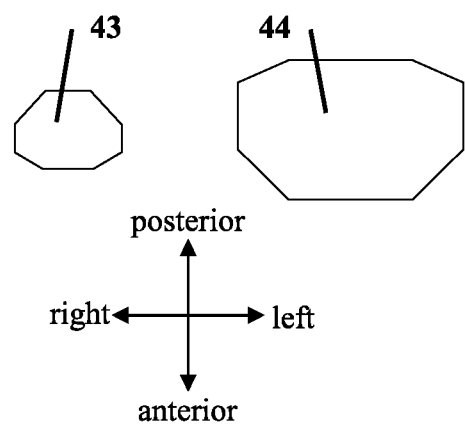

FIGS. 2k-o, especially FIG. 21, show that all four side surfaces of the outer perimeter of the inlay are slightly angled. There is an angle 20 in the posterior side surface of the outer perimeter, an angle 21 in the anterior side surface of the outer perimeter, an angle 22 in the right side surface of the outer perimeter, and an angle 23 in the left side surface of the outer perimeter. As will be explained below, these angles provide a small amount of clearance that is needed for allowing a combined axial rotation of the inlay 3 and the upper sliding partner 1 around the longitudinal axis.

FIGS. 3a-d show the prosthesis with maximum extension. It is clearly visible that a further extension is prevented because several surfaces get in contact with each other: the back side of the protuberance 4 contacts the corresponding surface of the cut-out of the inlay 6 (thus closing the posterior gap 10 and widening the anterior gap 9), and the edges 18 and 19 of the upper and lower sliding partners 1, 2 get in contact with each other.

FIGS. 4a-d show the prosthesis with maximum flexion. Again, further flexion is prevented by the fact that a side surface of the protuberance 4 gets in touch with the corresponding surface of the inner perimeter the inlay 3 (thus closing the anterior gap 9 and widening the posterior gap 10), and the edges 18 and 19 of the upper and lower sliding partners 1, 2 touch each other.

FIGS. 5a-d show the prosthesis in the state of maximum right lateral bending. Further bending is inhibited as the right side surface the perimeter of the inlay touches the right side of the recess (thus closing the right lateral gap 15 and widening the left lateral gap 16) and as the edges 18 and 19 of the upper and lower sliding partners 1, 2 touch each other.

In summary, during extension and flexion, the upper sliding partner 1 rotates around both the inlay 3 and the lower sliding partner 2 (compare FIGS. 3d and 4d). In contrast, during right and left lateral bending, both the upper sliding partner 1 and the inlay 3 rotate around the lower sliding partner 2 (compare FIG. 5d).

FIGS. 6a-e show the prosthesis in the state of maximum right axial or longitudinal rotation. Further axial rotation is inhibited by the fact that the posterior side of the perimeter of the inlay 3 touches the posterior side of the recess 7 and the anterior side of the perimeter of the inlay 3 touches the anterior side of the recess 7 (compare FIGS. 6b, c, and e). During axial rotation, both the upper sliding partner 1 and the inlay 3 rotate around the longitudinal axis. Like the centre of rotation for extension and flexion, the centre of axial rotation is also placed dorsally, closer to its physiological location (compare FIG. 6e).

Figure 7:
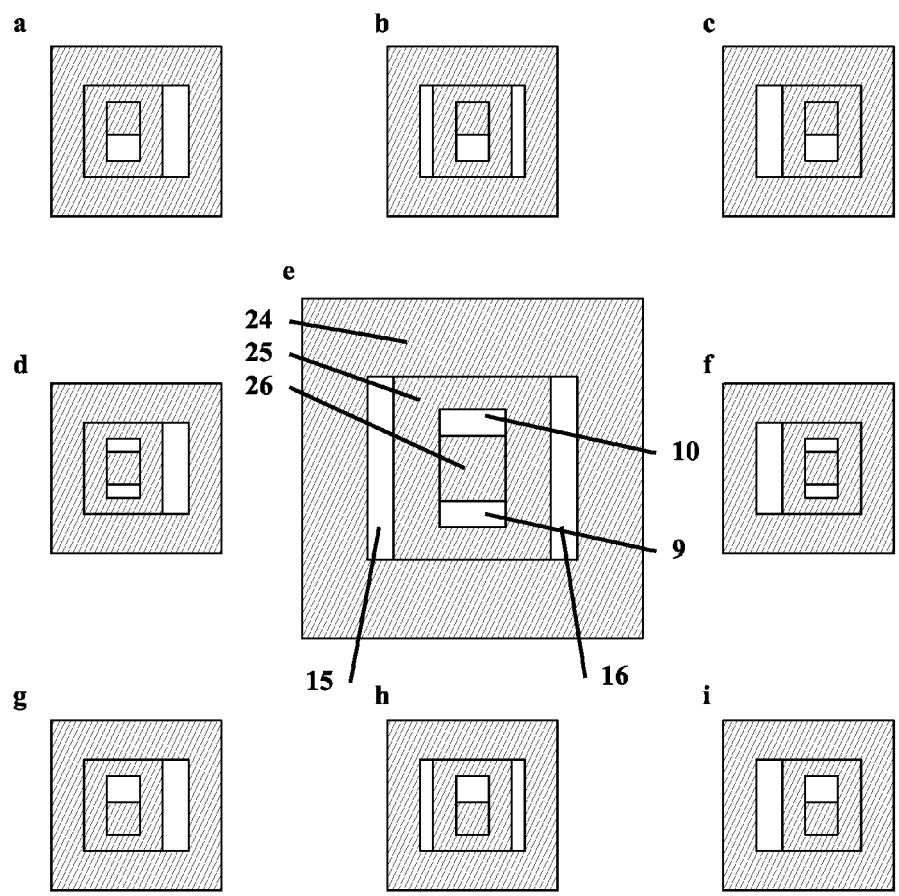
FIG. 7, 8, 9, 10, 11 Two-dimensional top view schemes of the side surfaces of the recess, the outer and inner perimeter of the inlay and the protuberance, including the different spaces in between depending on the direction of motion FIG. 12, 13 Prostheses without axial rotational limitation between the side surface of the inner perimeter of the inlay and of the protuberanc, and between the side surface of the recess and the outer perimeter of the inlay FIG. 14 Prosthesis with extended protuberance FIG. 15 Prosthesis with exchange of the position of recess and protuberance FIG. 16 Five-component prosthesis with additional middle sliding partner for lumbar spine FIG. 17-20 Means of fixation of upper and lower sliding partner with the vertebral body FIG. 21 Octagonal shape of endplates for cervical and lumbar spine

FIG. 7 shows (in two dimensions) schematically the basic construction of the prosthesis. There is an outer part 24 that corresponds to the lower sliding partner 2. The outer part 24 comprises (within an opening that corresponds to the recess 7) a middle part 25 that corresponds to the inlay 3. The middle part 25 finally comprises an inner part 26 that corresponds to the protuberance 4. The anterior and posterior gaps 9 and 10 and the lateral gaps 15 and 16 correspond to the gaps shown in the preceding figures. If the outer part 24 is fixed in space, both the middle 25 and the inner part 26 can only translate within certain limits. An upward translation of the inner part 26 corresponds to an extension of the prosthesis, and a downward translation to a flexion. Lateral translations of both the middle 25 and the inner 26 part correspond to right and left lateral bending of the prosthesis. As can be seen in FIGS. 7a-i all combinations of the different translations are possible. However, in contrast to the prosthesis that was described before, no axial rotations are possible.

Figure 8:
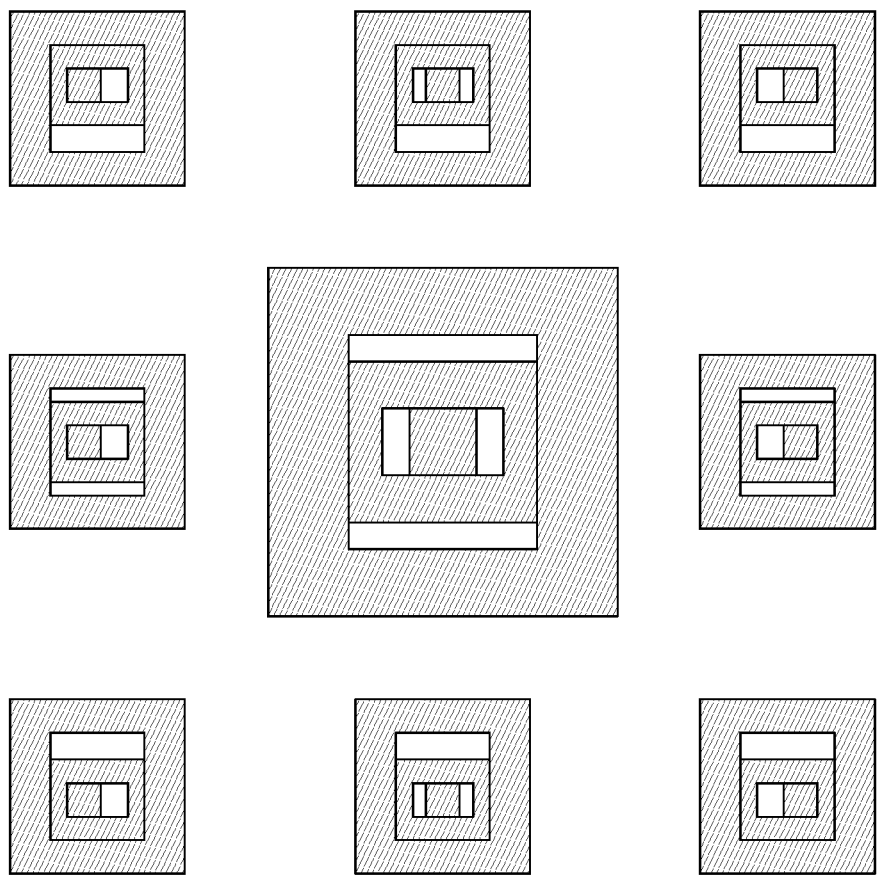

FIG. 8 shows the same principle of construction as FIG. 7. However, all parts have been rotated by 90°. Now, lateral translations of the inner part 26 would correspond to lateral bending, and upward and downward translations of the inner part 26 and the middle part 25 together would correspond to extension and flexion.

FIG. 9 finally shows an exact two-dimensional scheme of the prosthesis that has been described before. Now, the middle part 25 has angled side surfaces, allowing a limited axial rotation of the middle part 25 within the outer part 24. The four angles 20-23 correspond to the angles of the inlay 3 shown in FIG. 21. Obviously, the middle 25 and inner part 26 can only rotate together, as there is no room for the inner part 26 to rotate separately. Furthermore, the middle part 25 can only translate horizontally within the outer part 24, and the inner part 26 can only translate vertically within the middle part 25. As a result, the amounts of horizontal and vertical translation as well as axial rotation of the inner 26 and middle part 25 can all be defined and limited independently. Thus, the amounts of extension, flexion, lateral bending and axial rotation allowed by the prosthesis can also be defined and limited independently. The eight bottommost pictures of FIG. 9 show various possibilities of combined translations and rotations of the inner 26 and middle part 25. As can be seen, upwards and downwards translations are independent of lateral translations, and both types of translation are independent of axial rotations.

FIG. 10 shows another scheme that allows the amounts of possible translations and rotations to be defined independently. Here however, it is the inner part 26 which can both translate and rotate within the middle part 25.

FIG. 11 shows yet another similar possibility. This time, both the inner 26 and the middle part 25 are allowed to rotate.

Figure 12:
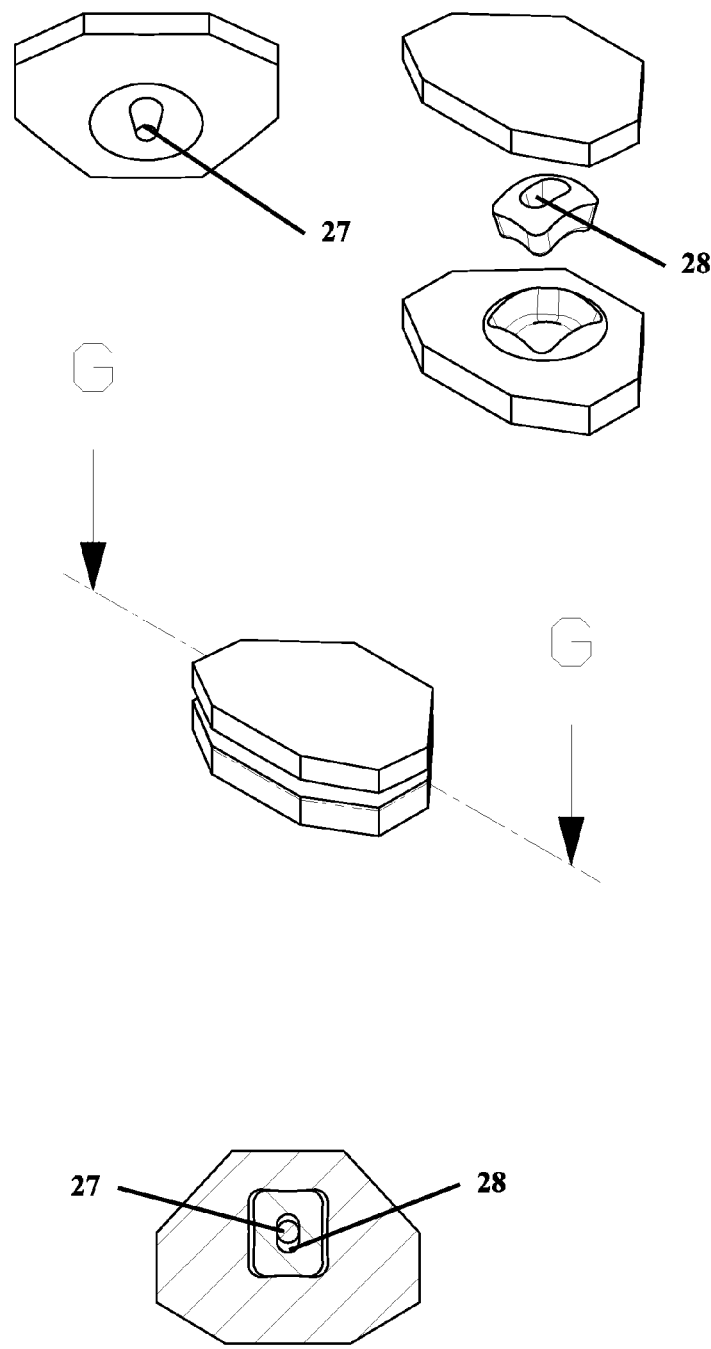

FIG. 12 shows a prosthesis which does no longer limit the axial rotation around the longitudinal axis. In this prosthesis, the protuberance, which was roughly shaped like the frustum of a pyramid before, is now shaped like the frustum of a cone 27. Furthermore, the cut-out 28 in the inlay has been adapted for acceptance of the new shape of the protuberance 27.

Figure 13:
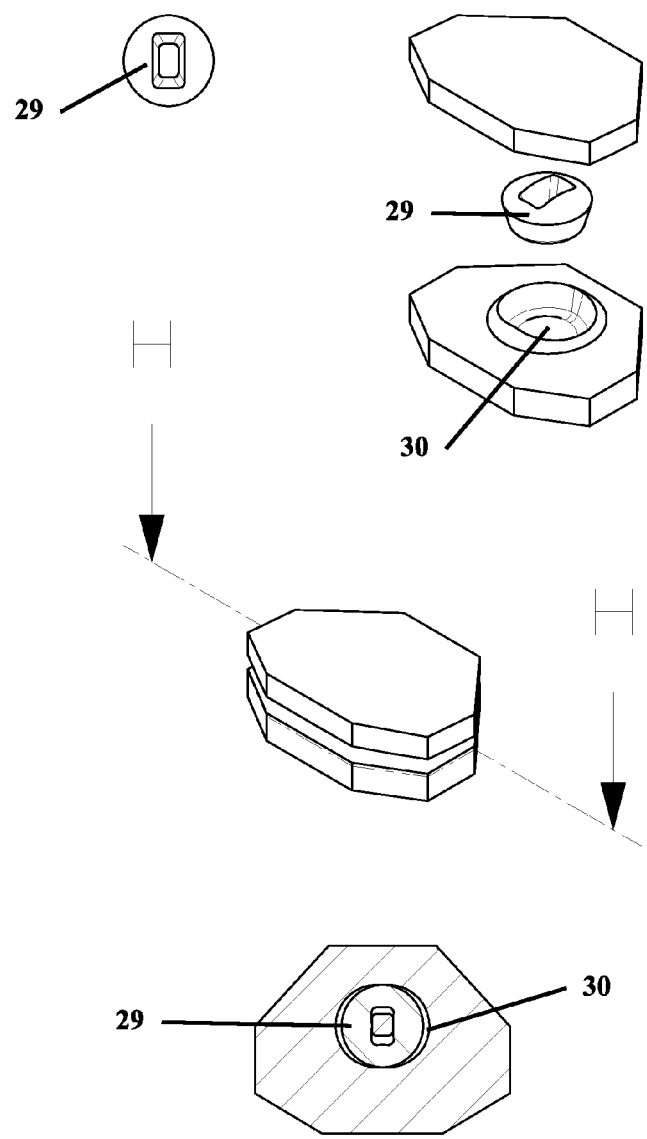

In FIG. 13, a similar construction is depicted. Here, the outer perimeter of the conical inlay 29 is shaped like the frustum of a cone, and the shape of the recess 30 in the lower sliding partner 2 has been adapted accordingly. As before, this construction does not limit the axial rotation.

FIG. 14 shows a prosthesis that is very similar to the prosthesis shown in FIGS. 1-6. The major difference is that the length of the protuberance has been maximized in FIG. 14. The tip of the extended protuberance 31 now lies within a separate recess, a hole, 32 in the original recess 7, increasing the total vertical overlap of the upper and lower sliding partner 1, 2 for even more safty of the prosthesis against luxation.

FIG. 15 shows a prosthesis, where the places of the protuberance 4 and the recess 7 have been exchanged. Here, the recess 33 is placed into the concavity 5 of the upper sliding partner 1, and the protuberance 34 is part of the convexity 8 of the lower sliding partner 2. However, the functions of the recess 33, the protuberance 34 and the inlay 3 remain the same and this prosthesis is also based on the construction scheme shown in FIG. 9 et sqq.

FIG. 16 shows a prosthesis for the lumbar spine comprising five parts: an upper 35 and a lower 36 sliding partner each having a protuberance 4, two identical inlays 3 and a single middle sliding partner 37 having two identical recesses 7, one on its upper and one on its lower side. If this prosthesis would be split in half by a horizontal plane lying in the centre of the middle sliding partner 37, one would essentially get two identical prostheses that would look very similar to the prostheses shown in FIGS. 1-6. Thus, the upper and lower sliding partner 35 and 36 correspond to the upper and lower sliding partner 1, 2 of the previous prosthesis, and the upper and lower surfaces of the middle sliding partner 37 correspond to the inner sides of the upper and lower sliding partner 1, 2 of the previous prosthesis. A notable difference in this prosthesis is the form of the edge 38 of the middle sliding partner 37 that has the shape of a dovetail (as can be seen in the two section views), i.e. its vertical thickness increases continuously in the direction of the periphery. The edges of the upper and lower sliding partners 35 and 36 are formed accordingly, i.e. their thicknesses decrease in the direction of the periphery.

FIGS. 17-20 show different means of providing a good fixation between sliding partners and adjacent vertebrae. In FIG. 17, a cross-like process is shown. Both the latero-lateral 39 and antero-posterior arm 40 of the cross are shaped like arcs, i.e. they are higher in their middles than at their ends, according the often concave shaped endplates of the vertebral bodies. The latero-lateral cross arm 39 is slightly higher than the anteroposterior arm 40, to have a step by step cutting through the bone of the vertebral endplates for making fixation easier and safer. It is more important to avoid an anteroposterior luxation of the prosthesis compared to a latero-lateral dislocation of the prosthesis, so that the cross arm from the right to the left is slightly higher.

Figure 18:
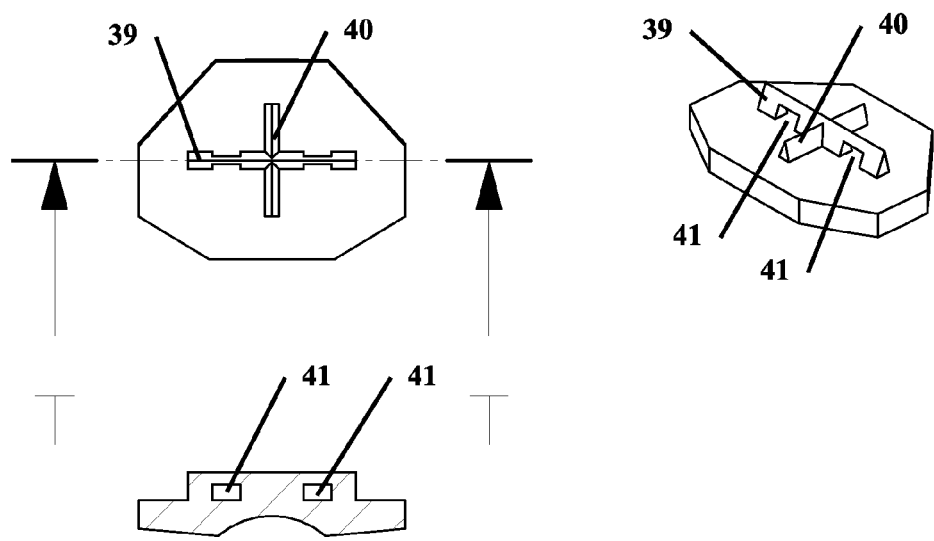

FIG. 18 shows a similar construction. The latero lateral arm 39 is still slightly higher than the antero posterior arm 40. Additionally, there are now two holes 41 in the laterolateral arm 39 for the acceptance of instruments during implantation of the prosthesis. Said means for the acceptance of instruments facilitate also explanation and an exact positioning of a sliding partner.

Figure 19:
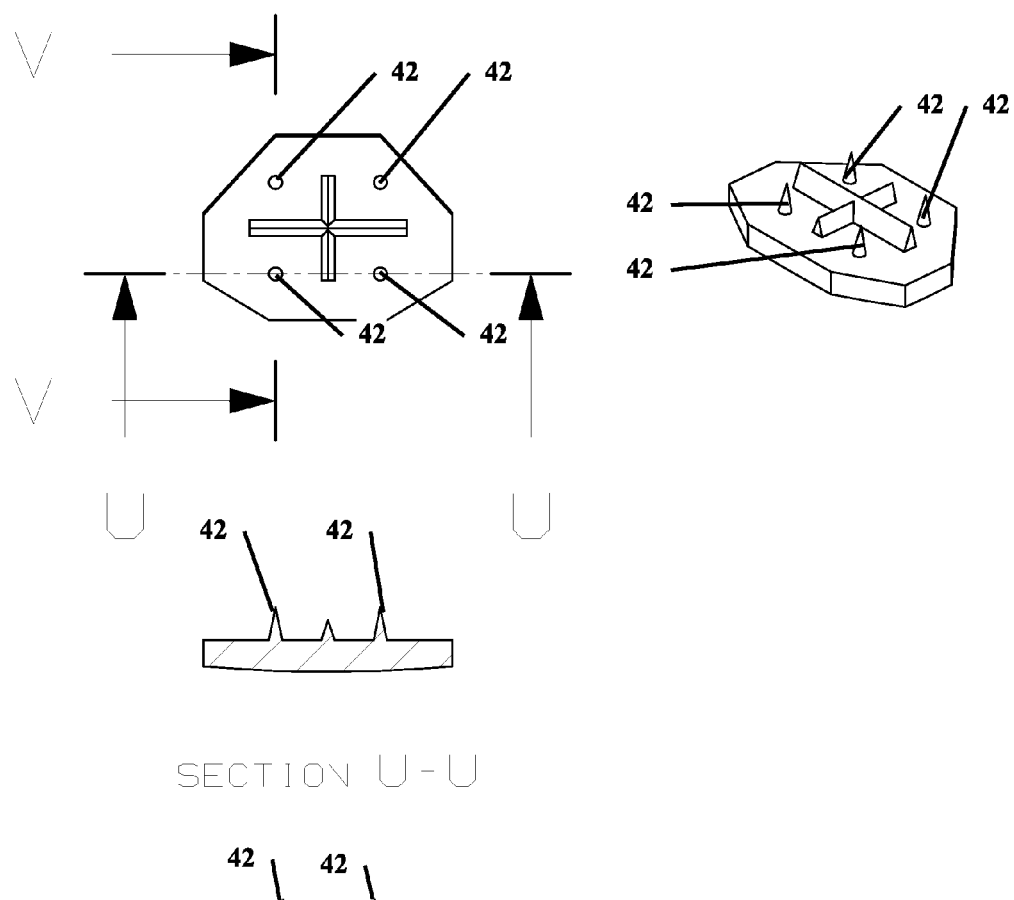
Figure 20:
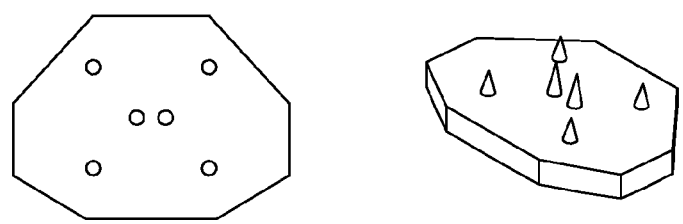

FIG. 19 shows a means of fixation comprising a cross-like process and four spikes 42. Finally, FIG. 20 shows the outer face of a sliding partner having six spikes 42, with the two spikes 42 in the centre being slightly longer than the spikes 42 in the periphery to compensate the concave shape of the endplate of a vertebral body.

FIG. 21 shows the octagonal shapes of two prosthesis endplates. The smaller shape 43 is intended for use in cervical implants, and the larger shape 44 for use in lumbar implants. The four relevant anatomical directions are indicated in the figure. The shapes of the prosthesis endplates are designed to both yield a large contact area between prosthesis endplates and adjacent vertebrae endplates and to be geometrically simple. Partial plane sides facilitate fixation of instruments for implantation via anterior, antero-lateral (lumbar spine only) and lateral (lumbar spine only) approach.

REFERENCE NUMBER LIST 1 upper sliding partner
2 lower sliding partner
3 inlay
4 protuberance
5 concavity
6 cut-out of the inlay
7 recess
8 convexity
9 anterior gap
10 posterior gap
11 upper side of the inlay
12 lower side of the inlay
13 tip of the protuberance
14 bottom of the recess
15 right lateral gap
16 left lateral gap
17 side surfaces of the recess
18 edge of the upper sliding partner
19 edge of the lower sliding partner
20 angled posterior side surface of the outer perimeter of the inlay
21 angled anterior side surface of the outer perimeter of the inlay
22 angled right side surface of the outer perimeter of the inlay
23 angled left side surface of the outer perimeter of the inlay
24 outer part (corresponds to lower sliding partner with recess)
25 middle part (corresponds to inlay)
26 inner part (corresponds to protuberance)
27 conical protuberance
28 cut-out of the inlay, adapted for conical protuberance
29 conical inlay
30 recess, adapted for conical inlay
31 extended protuberance
32 hole in the bottom surface of the recess for acceptance of the tip of the extended protuberance
33 recess in concavity
34 protuberance in convexity
35 upper sliding partner of 5-part prosthesis
36 lower sliding partner of 5-part prosthesis
37 middle sliding partner of 5-part prosthesis
38 edge of middle sliding partner of 5-part prosthesis
39 latero-lateral cross arm
40 antero-posterior cross arm
41 hole in latero-lateral cross arm
42 spike
43 endplate of cervical prosthesis
44 endplate of lumbar prosthesis

The invention claimed is:

1. Intervertebral disc prosthesis for the total replacement of an intervertebral disc within the cervical or lumbar spine, comprising a first and a second sliding partner with means on the outer sides to firmly assemble with adjacent upper and lower vertebral bodies and a convexity with an articulation surface on the inner side of said first or second sliding partner and a concavity with an articulation surface on the inner side of the respective other sliding partner, wherein
  a. one of said articulating convexity or concavity has a recess with four side surfaces and a bottom articulation surface; and
  b. the respective other articulating convexity or concavity has a fixed protuberance with four side surfaces and an articulation tip surface wherein the protuberance is surrounded by the respective articulation surface of the convexity or the concavity; and
  c. an inlay comprises four outer side surfaces facing the four side surfaces of the recess and a cut-out comprising four inner side surfaces facing the four side surfaces of the engaging protuberance; and
  d. the inlay has on one side a convex articulation surface and on the opposite side a concave articulation surface each conjoined with the four outer and four inner side surfaces, wherein one articulation surface has an identical radius of curvature with the articulation surface on which the protuberance is fixed and on the opposite side the other articulation surface has an identical radius of curvature with the bottom articulation surface of the recess; and
  e. the inlay is movable arranged within the articulating surfaces of both sliding partners; and
  f. a range of motion between the first and second sliding partners in relation to each other around a sagittal, frontal and longitudinal axis is defined by
    i. the radii of curvature of the convex and concave articulation surfaces;

ii. a size and shape of the recess, of the inlay including its cut-out and of the protuberance; and iii. a clearance between the side surfaces of the recess and the outer side surfaces of the inlay; and iv. a clearance between the inner side surfaces of the inlay and the side surfaces of the protuberance.

2. Intervertebral disc prosthesis according to claim 1, wherein at least one of convexity or concavity of first or second sliding partner are partly or completely surrounded by an edge which is designed to limit motion and to maximize the contact area at final ranges of motion in each direction around the sagittal and frontal axes.

3. Intervertebral disc prosthesis according to claim 1 or 2, wherein the edges are made of a flexible material enabling soft limitation at final ranges of motion in each direction around the sagittal and frontal axes.

4. Intervertebral disc prosthesis according to claim 1, wherein the shape of the recess, of the inlay and of the protuberance is rectangular, round, cylindrical, pyramidal, conical including a truncated pyramid and conus, or a combination of the aforementioned shapes.

5. Intervertebral disc prosthesis according to claim 1, wherein the shape of the side surfaces of the recess, the shape of the outer and inner side surfaces of the inlay and the shape of the side surfaces of the protuberance is planar, curved, angled or round or a combination thereof.

6. Intervertebral disc prosthesis according to claim 1, wherein the articulation surfaces of the convexity and corresponding concavity have a spherical, cylindrical, toroidal, helical and/or conical shape or a combination thereof.

7. Intervertebral disc prosthesis according to claim 1 or 2, wherein size and shape of the recess and of the outer side surfaces of the inlay are constructed in such a manner that a limited rotation of first and second sliding partners around either a sagittal or frontal axis is possible.

8. Intervertebral disc prosthesis according to claim 7, wherein size and shape of the recess and of the outer side surfaces of the inlay are constructed in such a manner that a limited rotation of first and second sliding partners around a longitudinal axis is possible.

9. Intervertebral disc prosthesis according to claim 1 or 2, wherein size and shape of the inner side surfaces of the inlay and of the side surfaces of the protuberance are constructed in such a manner that a limited rotation of first and second sliding partners around either a sagittal or frontal axis is possible.

10. Intervertebral disc prosthesis according to claim 9, wherein size and shape of the inner side surfaces of the inlay and of the side surfaces of the protuberance are constructed in such a manner that a limited rotation of first and second sliding partners around a longitudinal axis is possible.

11. Intervertebral disc prosthesis according to claim 1, wherein the shape of the recess and of the outer side surfaces of the inlay and/or the shape of the inner side surfaces of the inlay and of the side surfaces of the protuberance allows unlimited rotation of first and second sliding partners around the longitudinal axis.

12. Intervertebral disc prosthesis according to claim 1, wherein the tip articulation surface of the protuberance is convex or concave with a radius of curvature corresponding to the concave or convex curvature of the bottom articulation surface of the recess, enabling the articulation of the tip articulation surface with the bottom articulation surface of the recess.

13. Intervertebral disc prosthesis according to claim 1, wherein the tip articulation surface of the protuberance is articulating with a surface arranged within a hole below the bottom articulation surface of the recess, and the tip articulation surface of the protuberance has the same radius of curvature as the facing articulation surface the hole.

14. Intervertebral disc prosthesis according to claim 1 or 2, wherein the first and/or second sliding partners and/or the inlay comprise different materials or are coated differently.

15. Intervertebral disc prosthesis according to claim 1 or 2, wherein the first and second sliding partners and/or the inlay are constructed in one piece or are firmly, but reversibly assembled of at least two pieces.

16. Intervertebral disc prosthesis according to claim 1 or 2, wherein the inlay and/or at least one of the first and second sliding partners or a part of them are made of a flexible material to damp an intervertebral shock or applied load.

17. Intervertebral disc prosthesis according to claim 1 or 2, wherein the first and/or second sliding partners have on their outer surfaces for assembly with a vertebral body at least one cross-shaped anchor.

18. Intervertebral disc prosthesis according to claim 17, providing at least one cross-shaped anchor in combination with anchoring teeth.

19. Intervertebral disc prosthesis according to claim 1 or 2, wherein a middle sliding partner with an upper and lower articulation surface positioned between the articulation surfaces of the first and second sliding partners comprises articulating concavities on its upper and lower articulation surfaces, resulting in an upper and a lower articulation area, wherein at least one of said upper and lower articulation areas comprises the recess, the fixed protuberance and the inlay to limit the range of motion between the articulating sliding partners in relation to each other around a sagittal, frontal and longitudinal axis defined by i. the radii of curvature of the convex and concave articulation surfaces;

ii. a size and shape of the recess, of the inlay including its cut-out and of the protuberance;

iii. a clearance between the side surfaces of the recess and the outer side surfaces of the inlay; and iv. a clearance between the inner side surfaces of the inlay and the side surfaces of the protuberance.

20. Intervertebral disc prosthesis according to claim 19, wherein the articulation areas above and below the middle sliding partner are constructed differently.

21. Intervertebral disc prosthesis according to claim 19, wherein the articulation areas above and below the middle sliding partner are constructed equally.

22. Intervertebral disc prosthesis according to claim 1 or 2, wherein the first and/or second sliding partners and/or the inlay comprise the same materials or are coated with the same materials.

* * * * *